United States Patent [19]

Giesecke et al.

[11] 4,386,213
[45] May 31, 1983

[54] DI- AND OLIGO-1,2,4-TRIAZOLIDINE-3,5-DIONES AND PROCESSES FOR THEIR PRODUCTION

[75] Inventors: Henning Giesecke, Cologne; Rudolf Merten, Leverkusen; Ludwig Rottmaier, Odenthal, all of Fed. Rep. of Germany

[73] Assignee: Bayer Aktiengesellschaft, Leverkusen, Fed. Rep. of Germany

[21] Appl. No.: 278,647

[22] Filed: Jun. 29, 1981

[30] Foreign Application Priority Data

Jul. 21, 1980 [DE] Fed. Rep. of Germany ....... 3027611

[51] Int. Cl.³ .......................................... C07D 249/12
[52] U.S. Cl. .................................................... 548/264
[58] Field of Search ......................................... 548/264

[56] References Cited

U.S. PATENT DOCUMENTS

| | | | |
|---|---|---|---|
| 3,141,023 | 7/1964 | Bousquet | 424/269 |
| 3,663,564 | 5/1972 | Jacobson et al. | 260/308 C |
| 3,966,530 | 6/1976 | Cutts et al. | 548/264 |
| 4,105,417 | 8/1978 | Coon | 44/63 |

FOREIGN PATENT DOCUMENTS 2342929   3/1974   Fed. Rep. of Germany .

OTHER PUBLICATIONS

Walk et al.; Chem. Ber., vol. 111 (10), pp. 3519–3523 (1978).
Zinner et al.; Chem. Abs., vol. 64:11202f (1966).
Coon; Chem. Abs., vol. 90: P74213b, (U.S. 4,105,417) 1978, (Index also Provided).

Primary Examiner—Mary C. Lee
Attorney, Agent, or Firm—Connolly and Hutz

[57] ABSTRACT

New di- or oligo-1,2,4-triazolidine-3,5-diones corresponding to the following Formula I:

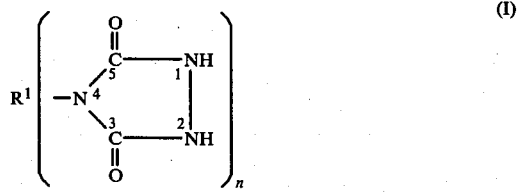

in which
$R^1$ represents a difunctional to pentafunctional organic radical, optionally substituted and/or interrupted by hetero atoms or hetero atom groups
and n=a number of from 2 to 5.

The compounds of Formula I are obtained by reaction of 0.9 and 1.1 Mole hydrazodicarbonamide or 1,2,4-triazolidine-3,5-dione with 1/n mole of an amine of the formula $R^1$ $(NH_2)_n$ by elimination of ammonia or by reaction of a monosubstituted hydrazodicarbonamide of the formula $(H_2N-CO-NH-NH-CO-NH)_n R^1$ by elimination of ammonia. $R^1$ and n have always the same meaning as in Formula I. The di- and oligo-1,2,4-triazolidine-3,5-diones are valuable starting materials for the production of in 1,2-position oxalkylated or glycidyl group containing intermediates for the production of polymers.

2 Claims, No Drawings

DI- AND OLIGO-1,2,4-TRIAZOLIDINE-3,5-DIONES AND PROCESSES FOR THEIR PRODUCTION

This invention relates to di- and oligotriazolidine-3,5-diones and to processes for their production.

The production of 1,2,4-triazolidine-3,5-dione from hydrazodicarbonamide and of 4-phenyl-1,2,4-triazolidine-3,5-dione from hydrazodicarbonamide and aniline hydrochloride is known. According to Liebigs Ann. 283, 41 (1894), it is carried out by heating hydrazodicarbonamide in the melt. However, this method is not suitable for working on an industrial scale. The melt obtained is heavily contaminated and, after cooling, accumulates in the form of a solid, hard mass which has to be size-reduced and purified. The yields of 1,2,4-triazolidine-3,5-dione amount to between 40 and 50% of the theoretical. In the reaction of hydrazodicarbonamide with aniline hydrochloride, 4-phenyl-1,2,4-triazolidine-3,5-dione is only formed as a secondary product.

Another method of producing 1,2,4-triazolidine-3,5-diones is to cyclise alkoxy carbonyl semicarbazides, as described in Archiv der Pharmazie 294, 370 (1961). Hitherto, this process has not been successfully worked on an industrial scale on account of the high price of the starting compounds and the sensitivity to hydrolysis of the intermediate products. Alkylene-4,4'-bis-1,2,4-triazolidine-3,5-diones substituted in the 1,2-position by alkyl or aryl have hitherto only been obtained by alkylation of the corresponding 1,2,4-triazolidine-3,5-diones substituted in the 1,2-position [Archiv der Pharmazie 299, 81 (1966)]. However, this process cannot be applied to triazolidine-3,5-diones unsubstituted in the 1- and 2-position because these positions can also be alkylated.

The present invention provides new di- and oligo-1,2,4-triazolidine-3,5-diones corresponding to the following general formula (I):

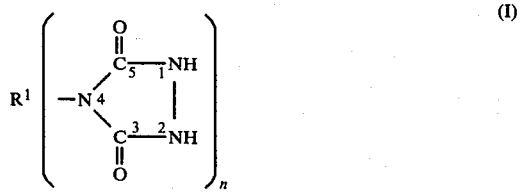

in which
$R^1$ represents a difunctional to pentafunctional unsubstituted or substituted, linear or branched aliphatic $C_2$–$C_{30}$, preferably $C_2$–$C_{12}$ radical, a difunctional to pentafunctional unsubstituted or substituted cycloaliphatic $C_5$–$C_{21}$ radical, a difunctional to pentafunctional unsubstituted or substituted aliphatic-aromatic $C_7$–$C_{17}$, preferably $C_7$–$C_{10}$ radical, a difunctional to pentafunctional unsubstituted or substituted aromatic $C_6$–$C_{21}$, preferably $C_6$–$C_{15}$ radical, the aliphatic radicals mentioned above optionally being interrupted by one or more oxygen atoms or tertiary nitrogen atoms and the polynuclear aliphatic-aromatic, polynuclear cycloaliphatic and polynuclear aromatic radicals mentioned above optionally being interrupted by at least one alkylene group containing from 1 to 4 carbon atoms, by at least one oxygen atom or tertiary nitrogen atom or by at least one sulfonyl group

and
n is a number of from 2 to 5, preferably 2 or 3.

Preferred substituents for $R^1$ are alkoxy carbonyl groups preferably containing from 1 to 4 carbon atoms in the alkoxy group, CN, $NO_2$, alkyl mercapto groups containing from 1 to 4 carbon atoms in the alkyl group, dialkylamino groups preferably containing from 1 to 6 carbon atoms in each alkyl group, halogens (preferably fluorine, chlorine, bromine) and, in the case of the aromatic radicals, lower alkyl groups preferably containing from 1 to 4 carbon atoms, in addition to the substituents mentioned above.

Compounds of formula (I) in which the radical $R^1$ is unsubstituted are particularly preferred.

Preferred radicals $R^1$ correspond for example to the following formulae:

1. —$(CH_2)_x$—   x=2–20, preferably 2–12

2. 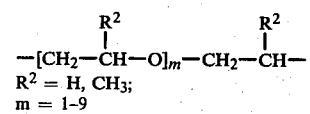
   $R^2$ = H, $CH_3$;
   m = 1–9

3. 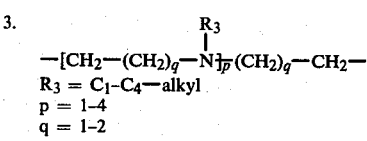
   $R_3$ = $C_1$–$C_4$—alkyl
   p = 1–4
   q = 1–2

4. 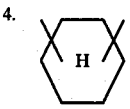

5. 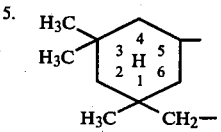

6. 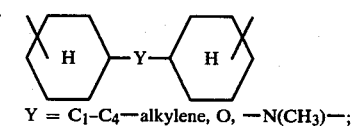
   Y = $C_1$–$C_4$—alkylene, O, —N($CH_3$)—;

7. 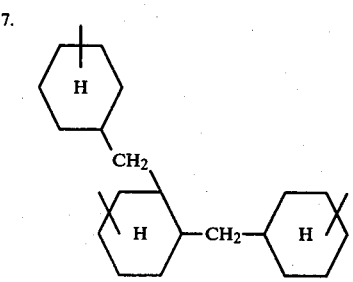

8. 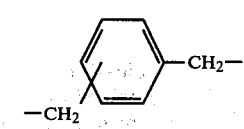

9. 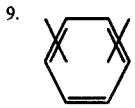

10. 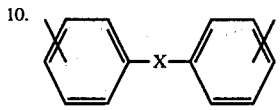

X = C₁-C₄—alkylene, O, —N(CH₃)—,

The di- and oligo-1,2,4-triazolidine-3,5-diones of the general formula (I) according to the invention may be obtained by various methods.

Thus, diamines and polyamines corresponding to the following formula (II):

$$R^1(NH_2)_n \quad (II)$$

in which $R^1$ and n have the same meaning as in formula (I), may be converted with hydrazodicarbonamide (process 1) or with 1,2,4-triazolidine-3,5-dione (process 2) into the di- and oligo-1,2,4-triazolidine-3,5-diones of general formula (I) at elevated temperatures, preferably in the presence of a solvent or solvent mixture, the reaction being accompanied by the elimination of ammonia. 1/m Mole of the diamine or polyamine (m=number of primary NH₂-groups per molecule) is preferably reacted with 0.9–1.1 moles of hydrazodicarbonamide or with 0.9–1.1 moles of 1,2,4-triazolidine-3,5-dione.

In another process (process 3), N-monosubstituted hydrazodicarbonamides corresponding to the following formula (III):

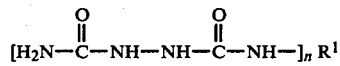

in which $R^1$ and n have the same meaning as in formula (I), are cyclised under the same conditions as described for processes 1 and 2 to form the di- and oligo-1,2,4-triazolidine-3,5-diones of formula (I), the reaction being accompanied by the elimination of ammonia.

The hydrazodicarbonamide used in process 1 is known from the literature and is obtained in a substantially quantitative yield in the reaction of 1 mole of hydrazine with 2 moles of urea in an aqueous medium with elimination of ammonia. The hydrazodicarbonamide obtained as a deposit is isolated by filtration under suction and may be immediately further processed as a filter-moist product providing the residual water can be removed during the cyclisation reaction. Dried hydrazodicarbonamide may of course also be used for the further reaction. It is also possible, following the addition of a suitable solvent to the resulting suspension of hydrazodicarbonamide in water, to distill off the water by heating and to react the hydrazodicarbonamide left behind with amines to form the 1,2,4-triazolidine-3,5-diones of formula (I) according to the invention.

The triazolidine-3,5-dione used in process 2 is also known from the literature (cf. Liebigs Ann. 283, 41 (1894)).

The N-monosubstituted hydrazodicarbonamides of formula (III) used in process 3 are obtained by reacting semicarbazides with isocyanates corresponding to the following formula (IV):

$$R^1(NCO)_n \quad (IV)$$

in which $R^1$ and n have the same meaning as in formula (I).

In general, it is best to carry out the reaction of semicarbazide and isocyanate to form the monosubstituted hydrazodicarbonamides corresponding to formula (III) in a solvent or diluent, in which case the starting materials, in substantially equivalent quantitative ratios (1 mole of semicarbazide=1 NCO-group), may either be dissolved or only suspended. It is of course also possible to carry out the reaction in the absence of a solvent or diluent. Solvents suitable for the process are, for example, aromatic hydrocarbons, chlorinated aromatic hydrocarbons, benzonitrile, aliphatic hydrocarbons, esters and ketones. Particularly suitable solvents are toluene, xylene, mesitylene, chlorobenzene, dichlorobenzene, N-methyl pyrrolidone, dimethyl formamide, dimethyl acetamide, hexamethyl phosphoric acid triamide, tetramethyl urea, nitromethane and nitrobenzene. However, it is also possible to carry out the reaction at lower temperatures in water or lower alcohols.

The reaction may be carried out at temperatures of from −30° to +150° C. It is preferred to work at temperatures in the range of from −20° to +100° C. and particularly preferred to work at temperatures in the range of from −10° to +80° C.

The reaction mechanism by which each of the three variants of the process according to the invention takes place are immaterial. All three processes lead simply and reproducibly to high yields of the di- and oligo-1,2,4-triazolidine-3,5-diones of formula (I). It is possible that N-monosubstituted hydrazodicarbonamide corresponding to formula (III) is initially formed in process 1 from about 1 mole of hydrazodicarbonamide and 1/m mole of amine (m-number of primary amino groups per mole of amine) with elimination of 1 mole of ammonia, or in process 2 from about 1 mole 1,2,4-triazolidine-3,5-dione and 1/m mole of amine with ring opening. The compounds of formula (I) are then obtained from this N-monosubstituted hydrazodicarbonamide of formula (III) through cyclisation with elimination of ammonia.

In all three processes for producing the compounds of formula (I), the reaction temperature is generally in the range of from 150° to 280° C., preferably in the range of from 170° to 250° C. and more particularly in the range of from 175° to 220° C. The higher the temperature, the faster the reaction, although the danger of undesirable secondary products being formed and decomposition of the solvent increase.

The reaction times are generally between 1 and 40 hours although they may even be longer or shorter in exceptional cases.

To accelerate the reaction, it may be advisable to add acid or basic catalysts. Metal alcoholates (for example sodium methylate, tin(II)octoate) and tertiary amines are particularly suitable.

The reaction pressure is normally in the range of from 50 mbars to 5 bars. If the reaction is carried out at a pressure higher than atmospheric pressure, the ammonia formed has to be periodically let off so that the cyclisation reaction is preferably carried out under a pressure of from 300 mbars to 2 bars.

It can be advantageous to keep the concentration of ammonia eliminated in the reaction vessel at a low level. This can be done by any known method, for example by blowing out with an inert gas, such as air, nitrogen, carbon dioxide or steam. Low-boiling solvents, for example aliphatic, aromatic, araliphatic hydrocarbons, their technical mixtures and chlorinated hydrocarbons preferably containing from 1 to 10 carbon atoms, such as cyclohexane, toluene, xylenes, petroleum ether or chloroform, which are pumped or introduced dropwise into the reactor in liquid form, may also be used for removing the ammonia. The partial pressure of the ammonia may also be reduced by filtration under suction, i.e. by applying sub-atmospheric pressure.

The organic solvents used in the reaction should show adequate thermal stability under the reaction conditions and should be chemically inert to hydrazodicarbonamides and triazolidine-3,5-diones. In addition, the boiling point of the solvent used should be high enough to ensure that the solvent does not distill off during the reaction.

The boiling points of the solvents at atmospheric pressure generally amount to at least 150° C. and preferably to between about 175° and 280° C. The solvents may be miscible, partly miscible or immiscible with water at room temperature.

Suitable solvents are (A) nitrogen-containing solvents N-substituted by phenyl or $C_1$–$C_8$-alkyl groups, for example N-substituted pyrrolidones, urethanes, cyclic urethanes or ureas, for example N-methyl pyrrolidone, ethyl phenyl urethane, 5-methyl-2-oxazolidone, tetramethyl urea; also polyethers, for example diethylene glycol diethyl ether, phenols such as cresols, halogen-substituted phenols and cresols, for example 4-chlorophenol; dialkyl sulfones and cyclic sulfones each containing a maximum of 12 carbon atoms, for example dimethyl sulfone or sulfolan; aromatic or araliphatic ethers, such as diphenyl ether and dibenzyl ether, high-boiling alcohols, for example ethylene glycol.

Other suitable solvents are (B) aliphatic, cycloaliphatic, aromatic and araliphatic hydrocarbons and their technical mixtures such as, for example, dodecane, decalin, trimethyl benzene, naphthalene, 1-methyl naphthalene, diphenyl methane, halogenated aliphatic, cycloaliphatic, aromatic and araliphatic hydrocarbons and their technical mixtures, such as dodecyl chloride, 1,2,4-trichlorobenzene, 1-chloronaphthalene and dichlorotoluene.

It is particularly preferred to use diphenyl ether, diphenyl methane, 1-methyl naphthalene, dialkyl sulfones and cyclic sulfones, particularly sulfolan, and N-methyl pyrrolidone.

The reaction mixtures with the polar solvents mentioned above in (A) obtained after cyclisation (reaction) may be mixed during cooling with solvents inert to triazolidine-3,5-diones, such as aliphatic, cycloaliphatic, araliphatic or aromatic hydrocarbons, for example cyclohexane, toluene, xylene, aliphatic or cycloaliphatic alcohols, for example butanol, cyclohexanol and ethers or esters derived therefrom, for example glycol monomethyl ether, butyl acetate, ketones, for example acetone or ethyl methyl ketone and, where water-miscible polar solvents are used, even water, so that the triazolidine-3,5-diones which crystallise out are obtained in relatively high yields and in relatively pure form. The additions may amount to as much as 500% by weight, based on polar solvent.

The processes described above are suitable both for batch working and also for continuous working. In continuous working, the cyclisation reaction is carried out in known manner, for example in cascades or in tube reactors. The batch variant is preferred.

The fact that the reaction takes place smoothly in process 1 as described above was surprising because the cyclisation of hydrazodicarbonamide in the presence of primary amines had been expected to give poorly separable mixtures of 1,2,4-triazolidine-3,5-dione and di- and oligo-1,2,4-triazolidine-3,5-diones corresponding to formula (I).

It was also surprising to find that the 1,2,4-triazolidine-3,5-dione (process 2) reacts with primary amines to form 4-substituted triazolidine-3,5-diones although it is characterised by considerable thermal stability.

The di- and oligo-1,2,4-triazolidine-3,5-diones corresponding to formula (I) are valuable starting materials for the production of temperature-resistant polymers. Polyhydroxy alkyl triazolidine-3,5-diones produced therefrom are used, for example, as crosslinking components in temperature-resistant electrical insulating lacquers, whereas corresponding polyglycidyl triazolidine-3,5-diones are used, for example, as crosslinkers in powder lacquers applied by electrostatic powder spraying. Di- and oligo-1,2,4-triazolidine-3,5-diones corresponding to formula (I) may also be used in photographic compositions.

The percentages quoted in the following Examples represent percentages by weight.

EXAMPLE 1

60 g of hydrazodicarbonamide and 29 g of 1,6-diaminohexane are stirred in 100 ml of sulfolan for 2 hours at 175° C. and for 9 hours at 200° C. A deposit is precipitated on cooling and is isolated by filtration under suction and recrystallised from water, giving 36 g (51% of the theoretical) of 1,6-hexanediyl-4,4'-bis-1,2,4-triazolidine-3,5-dione in the form of colourless crystals melting at 215° to 217° C.

|  |  | C | H | N |
|---|---|---|---|---|
| $C_{10}H_{16}N_6O_4$ | calculated | 42.25 | 5.67 | 29.51 |
| (284.3) | found | 42.5 | 5.7 | 29.2 |

EXAMPLE 2

600 g of hydrazodicarbonamide and 150 g of ethylene diamine are stirred in 500 ml of N-methyl pyrrolidone for 4 hours at 175° C. and for 20 hours at 200° C. A deposit is precipitated on cooling and is isolated by filtration under suction and washed with ethanol. 462 g (80% of the theoretical) of 1,2-ethanediyl-4,4'-bis-1,2,4-triazolidine-3,5-dione are obtained in the form of colourless crystals melting at >330° C.

|  |  | C | H | N |
|---|---|---|---|---|
| $C_6H_8N_6O_4$ | calculated | 31.58 | 3.53 | 36.83 |
| (228.2) | found | 31.4 | 3.6 | 36.8 |

IR (KBr): 1731, 1673 $cm^{-1}$ (C=O).

EXAMPLE 3

765 g of 1-aminomethyl-5-amino-1,3,3-trimethyl cyclohexane and 708 g of hydrazodicarbonamide are stirred in 1 liter of N-methyl pyrrolidone for 4 hours at 175° C., for 5 hours at 200° C. and for 15 hours at 220° C. The solvent is then distilled off in vacuo and the residue is dried in vacuo, giving 1473 g (97% of the theoretical) of 1-(3,5-dioxo-1,2,4-triazolidin-4-yl-methyl)-1,3,3-trimethyl-5-(3,5-dioxo-1,2,4-triazolidin-4-yl)-cyclohexane in the form of colourless crystals melting at 213 C. (decomposition).

IR (KBr): 1776, 1714, 1703 cm$^{-1}$ (C=O)
MS (m/e): mol. peak 338.

EXAMPLE 4

32 g of 2-(4-aminocyclohexylmethyl)-4,4'-diaminodicyclohexylamine and 36 g of hydrazodicarbonamide are stirred in 50 ml of N-methyl pyrrolidine for 4 hours at 175° C., for 3 hours at 200° C. and for 1 hour at 220° C. The solution is cooled and stirred into 1 liter of water. A deposit is precipitated and is isolated by filtration under suction and washed with water, giving 35 g (52% of the theoretical) of 2-[4-(3,5-dioxo-1,2,4-triazolidin-4-yl)-cyclohexylmethyl]-4,4'-bis-(3,5-dioxo-1,2,4-triazolidin-4-yl)-dicyclohexylmethane in the form of colourless crystals melting at 270° C. (decomposition).

EXAMPLE 5

420 g of 4,4'-diaminodicyclohexylmethane and 472 g of hydrazodicarbonamide are stirred in 750 ml of N-methyl pyrrolidone for 4 hours at 175° C., for 8 hours at 200° C. and for 4 hours at 220° C. The reaction product is cooled and subsequently stirred into 3 liters of water. A deposit is precipitated which is isolated by filtration under suction and washed with water, giving 566 g (75% of the theoretical) of 4,4'-bis-(1,2,4-triazolidine-3,5-dione-4-yl)-dicyclohexyl methane) in the form of colourless crystals melting at 305° C. (decomposition).
MS (m/e): mol. peak 378

EXAMPLE 6

A solution of 446 g of semicarbazide hydrochloride in 2 liters of water is neutralised with Na$_2$CO$_3$. 250 g of diphenyl methane-4,4'-diisocyanate dissolved in 400 ml of dioxane are then added dropwise with stirring over a period of 2 hours at room temperature. After stirring for 6 hours at 40° to 60° C., the deposit formed is isolated by filtration under suction and washed with water. The moist deposit is then suspended in 1 liter of sulfolan and the resulting suspension is heated to 160° C. until no more water distills off. A vacuum of 300 mbars is then applied, after which the suspension is stirred for 10 hours at 200° C. A deposit is formed on cooling which is isolated by filtration under suction and washed with methanol, giving 178 g of 4,4'-bis-(1,2,4-triazolidine-3,5-dione-4-yl)-diphenyl methane in the form of colourless crystals melting at 320° C.

IR (KBr): 1781 (shoulder), 1713 cm$^{-1}$ (c=o)
MS (m/e): mol. peak 366

EXAMPLE 7

102 g of 1,4-butane diol-bis-(3-aminopropylether) and 120 g of hydrazodicarbonamide are stirred in 300 ml of N-methyl pyrrolidone for 1 hour at 150° C., for 2 hours at 175° C. and for 5 hours at 200° C. A deposit is precipitated on cooling and is isolated by filtration under suction and thoroughly boiled with 200 ml of acetonitrile, leaving as a residue 142 g (76% of the theoretical) of 1,4-butane diol-bis-[3-(3,5-dioxo-1,2,4-triazolidin-4-yl)-propyl ether] in the form of colourless crystals melting at 152° to 154° C.

|  |  | C | H | N |
|---|---|---|---|---|
| C$_{14}$H$_{24}$N$_6$O$_6$ | calculated | 45.15% | 6.50% | 22.57% |
| (372.4) | found | 45.2% | 6.6% | 22.6% |

IR (KBr): 1768, 1674 cm$^{-1}$ (C=O)

EXAMPLE 8

100 g of 1,12-diaminododecane and 120 g of hydrazodicarbonamide are stirred in 300 ml of N-methyl pyrrolidone for 1 hour at 175° C. and for 4 hours at 200° C. A deposit precipitates on cooling and is isolated by filtration under suction and thoroughly boiled with 300 ml of acetonitrile, giving 156 g (85% of the theoretical) of 1,12-dodecane-4,4'-bis-1,2,4-triazolidine-3,5-dione in the form of colourless crystals melting at 172°–175° C.

|  |  | C | H | N |
|---|---|---|---|---|
| C$_{16}$H$_{28}$N$_6$O$_4$ | calculated | 52.16% | 7.66% | 22.81% |
| (368.5) | found | 52.2% | 7.7% | 22.6% |

MS (m/e): mol. peak 368

EXAMPLE 9

101 g of 1,2,4-triazolidine-3,5-dione and 57 g of 1,4-diaminocyclohexane are heated with stirring in 500 ml of N-methyl pyrrolidone for 4 hours at 175° C. and for 30 hours at 200° C. A deposit crystallises out on cooling and is isolated by filtration under suction, washed with ethanol and dried, giving 110 g (78% of the theoretical) of 1,4-cyclohexanediyl-bis-(1,2,4-triazolidine-3,5-dione-4-yl) in the form of colourless crystals melting at >300° C.

|  |  | C | H | N |
|---|---|---|---|---|
| C$_{10}$H$_{14}$N$_6$O$_4$ | calculated | 42.56% | 4.96% | 29.75% |
| (282.2) | found | 42.7% | 5.1% | 29.1% |

MS (m/e): mol. peak 282.

EXAMPLE 10

72.5 g of bis-(3-aminopropyl)-methylamine and 120 g of hydrazodicarbonamide are stirred in 300 ml of N-methyl pyrrolidone for 2 hours at 175° C. and for 3 hours at 200° C. The reaction product is concentrated in vacuo, dissolved in water and precipitated with isopropanol giving a colourless product which could not be crystallised. For characterisation and purification, the product is dissolved in water, the resulting solution is adjusted to pH 2 with concentrated HCl and subsequently concentrated in vacuo. The residue is recrystallised from ethanol, giving 112 g (65% of the theoretical) of bis-[3-(3,5-dioxo,1,2,4-triazolidin-4-yl)-propyl]-methylamine hydrochloride in the form of colourless crystals melting at 238° C.

IR (KBr): 1763, 1698 cm$^{-1}$ (C=O)

EXAMPLE 11

A solution of 89 g of semicarbazide hydrochloride in 250 ml of water is neutralised with Na$_2$CO$_3$. 101 g of 4,4'-diisocyanatodiphenyl ether dissolved in 100 ml of dioxane are then added dropwise with stirring over a period of 2 hours at room temperature. After stirring for 6 hours at 40° to 60° C., the deposit formed is isolated by filtration under suction and washed with acetone. The deposit is dried in air overnight and subsequently suspended in 600 ml of sulfolan. The suspension is heated at 160° C. until no more water distills off. A vacuum of 300 mbar is then applied, followed by stirring for 20 hours at 200° C.

The solvent is distilled off in vacuo and the residue is recrystallised from acetonitrile, giving 73.6 g (50% of the theoretical) of 4,4'-(bis-1,2,4-triazolidine-3,5-dione-4-yl)-diphenyl ether in the form of colourless crystals melting at 314° to 315° C.

$^1$H-NMR (d-DMSO): δ=6.8–7.7 ppm (m, 8H aromat.), 8.7 ppm (s, 4H).

EXAMPLE 12

64.2 g of hydrazodicarbonamide and 37 g of m-xylene diamine in 300 ml of N-methyl pyrrolidone are heated with stirring for 4 hours to 175° C. and for 30 hours to 200° C. The solvent is then distilled off in vacuo and the residue is recrystallised from chloroform, giving 58 g (70% of the theoretical) of 1,3-bis-(1,2,4-triazolidine-3,5-dione-4-yl-methyl)-benzene in the form of colourless crystals melting at 244° to 246° C.

IR (KBr): 1770 cm$^{-1}$ (shoulder), 1700 cm$^{-1}$ (C=O)
1H-NMR(dDMSO): δ=4.5 ppm (2, 2 CH$_2$), 7.2 ppm (2, 4H aromat.), 10.2 ppm (s, 4H).

APPLICATION EXAMPLE 388 g of terephthalic acid dimethyl ester, 202 g of 1,2-ethanediyl-4,4'-bis-[bis-(2-hydroxyethyl)-1,2,4-triazolidine-3,5-dione] and 62 g of 1,2-ethane diol are melted and 2 g of lead acetate, 1 g of titanium tetrabutylate and 50 ml of xylene are added to the resulting melt which is then heated for 8 hours to 190° C. After heating for 6 hours in a light vacuum to 220° C., the melt is condensed to completion over a period of 3 hours at 220° to 230° C. in a stronger vacuum. 518 g of a brown resin which is brittle at room temperature are obtained.

35 g of this resin are dissolved in 65 g of m-cresol, 1.6 g of a stabilised titanium tetrabutylate solution (prepared by heating 1 part by weight of titanium tetrabutylate and 2 parts by weight of cresol) are added to the resulting solution which is then applied to a degreased sheet of iron and stoved for 20 minutes at 200° C. and then for 10 minutes at 300° C. An elastic, firmly adhering film characterised by a smooth surface is obtained which does not crack or flake off when the sheet of iron is bent.

The 1,2-ethanediyl-4,4'-bis-[bis-(2-hydroxyethyl)-1,2,4-triazolidine-3,5-dione] used for producing the polyester is obtained as follows.

176 g of ethylene oxide are introduced into a suspension of 228 g of 1,2-ethanediyl-4,4'-bis-1,2,4-triazolidine-3,5-dione and 2 g of triethyl amine in 1 kg of dimethyl formamide over a period of 6 hours at 125° C. in such a way that no ethylene oxide escapes. Most of the solvent is removed by applying a vacuum of 40 mbar. The residue of 483 g obtained is dissolved under heat in 500 ml of a solvent mixture of 7 parts by volume of acetone and 3 parts by volume of isopropanol. A deposit is precipitated on cooling and is isolated by filtration under suction and dried in vacuo, giving 330 g of 1,2-ethanediyl-4,4'-bis-[bis-(2-hydroxyethyl)-1,2,4-triazolidine-3,5-dione] in the form of colourless crystals melting at 153° to 155° C.

| | | C | H | N |
|---|---|---|---|---|
| C$_{14}$H$_{24}$N$_6$O$_8$ | calculated | 41.58 | 5.98 | 20.78 |
| (404.4) | found | 41.4 | 5.7 | 20.9 |

I claim:
1. A di- or oligo-1,2,4-triazolidine-3,5-dione of the formula

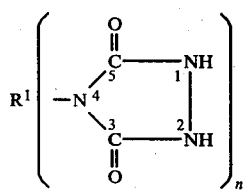

wherein
n is a number of from 2 to 5 and R$^1$ is selected from the group consisting of
(1) —(CH$_2$)$_{\overline{x}}$
wherein x is a number of from 2 to 20;

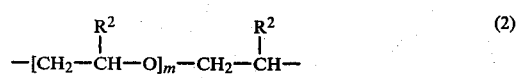

wherein R$^2$ is H or CH$_3$ and m is a number of from 1 to 9;

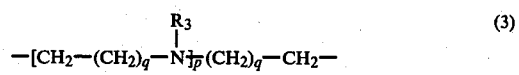

wherein R$_3$ is C$_1$–C$_4$-alkyl, p is a number of from 1 to 4 and q is a number of from 1 to 2;

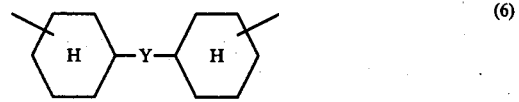

wherein Y is C$_1$–C$_4$-alkylene, O or —N(CH$_3$)—;

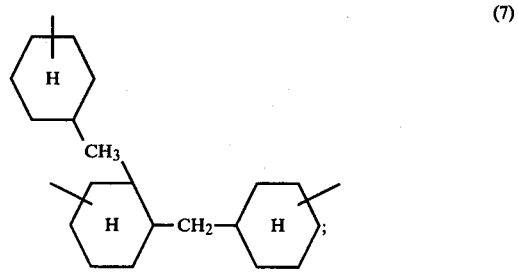

-continued
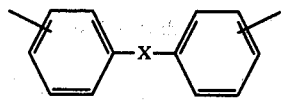
wherein X is $C_1$–$C_4$-alkylene, O or —N(CH$_3$)—;
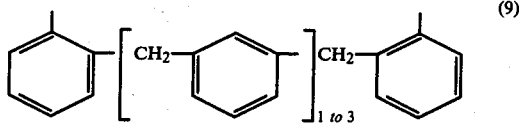
and
—(CH$_2$)$_3$—O—(CH$_2$)$_{2\ to\ 4}$—O—(CH$_2$)$_3$—.  (10)
2. A compound of claim 1 wherein R$^1$ is —(CH$_2$)$_6$— and n is 2.
* * * * *